(12) United States Patent
Lee

(10) Patent No.: US 12,186,167 B1
(45) Date of Patent: Jan. 7, 2025

(54) MEDICAL DEVICE FOR DRESSING HEAD WOUNDS

(71) Applicant: Joung Hoon Lee, Los Angeles, CA (US)

(72) Inventor: Joung Hoon Lee, Los Angeles, CA (US)

( * ) Notice: Subject to any disclaimer, the term of this patent is extended or adjusted under 35 U.S.C. 154(b) by 0 days.

(21) Appl. No.: 18/534,376

(22) Filed: Dec. 8, 2023

(51) Int. Cl.
*A61F 13/12* (2006.01)
*A61F 13/01* (2024.01)

(52) U.S. Cl.
CPC ........ *A61F 13/12* (2013.01); *A61F 13/01029* (2024.01); *A61F 13/01038* (2024.01)

(58) Field of Classification Search
CPC .... A61F 13/00; A61F 13/12; A61F 13/00021; A61F 13/00004; A61F 13/0273; A61F 2013/00102; A61F 2013/00089; A61F 5/24; A61F 5/28; A61F 5/30; A61F 5/32; A61F 5/05883; A61F 5/05891; A61F 5/3707; A61F 2007/0007; A61F 2007/0008; A61F 2007/0013; A61F 2007/0014; A61F 2007/0002; A61H 2205/02; A61H 2205/025; A45D 44/22
USPC ...... 602/17, 41, 53, 74, 75, 60, 61; 607/108, 607/109, 110; 606/204.15; 128/97.1, 128/106.1, 112.1, 857
See application file for complete search history.

(56) References Cited

U.S. PATENT DOCUMENTS

| | | | |
|---|---|---|---|
| 3,741,202 A * | 6/1973 | Morgan | A61F 13/122 606/204.35 |
| 5,031,609 A | 7/1991 | Fye | |
| 6,554,787 B1 | 4/2003 | Griffin et al. | |
| 2002/0052569 A1 * | 5/2002 | Horning | A61F 7/10 602/41 |
| 2009/0177134 A1 | 7/2009 | Timothy | |

(Continued)

FOREIGN PATENT DOCUMENTS

| CN | 205198268 U | 5/2016 |
|---|---|---|
| CN | 206491936 U | 9/2017 |
| KR | 102499844 B1 | 2/2023 |

OTHER PUBLICATIONS

Post Surgical Chin Strap Bandage for Women—Neck and Chin Compression Garment Wrap—Face Slimmer, Jowl Tightening; V T Variteks; Available at: https://www.amazon.com/Post-Surgical-Strap-Bandage- Women/dp/B07PZSLCD8?th=1 (Last Visited: Sep. 6, 2023).

(Continued)

*Primary Examiner* — Caitlin A Carreiro
(74) *Attorney, Agent, or Firm* — Wentsler LLC

(57) ABSTRACT

A medical device for dressing head wounds of a patient. The device has a dome-shaped flexible cap with a circumferential pocket around its base and an adjustable strap having two opposite ends, wherein the two opposite ends can be affixed to the flexible cap using an attachment mechanism. The adjustable strap is further adapted to cover the patient's chin, thereby securing the flexible cap over the patient's head. The adjustable strap can further have a chin pocket at a middle portion of the strap such that it overlays the patient's chin. The circumferential pocket and the chin pocket are configured to accommodate at least one wound dressing pad for covering the head wounds, wherein the head wounds are located at least partially in front, back, and/or below the patient's ears and at least partially on the patient's chin.

20 Claims, 5 Drawing Sheets

(56) References Cited

U.S. PATENT DOCUMENTS

| | | | |
|---|---|---|---|
| 2009/0299259 A1 | 12/2009 | Cumming et al. | |
| 2010/0016775 A1* | 1/2010 | Cumming | A61F 13/12 602/60 |
| 2012/0296252 A1 | 11/2012 | Cumming et al. | |
| 2014/0288476 A1 | 9/2014 | Wright et al. | |
| 2016/0374864 A1 | 12/2016 | Ahmed | |
| 2017/0000651 A1 | 1/2017 | Cumming et al. | |
| 2017/0246041 A1* | 8/2017 | Cumming | A61F 13/12 |
| 2018/0263824 A1* | 9/2018 | Ible | A61F 13/01029 |
| 2020/0206035 A1 | 7/2020 | Kantor et al. | |

OTHER PUBLICATIONS

Post Surgical Chin Strap Bandage for Women—Neck and Chin Compression Garment Wrap—Face Slimmer, Jowl Tightening, Chin Lifting; Aurafix Orthopedic Products, Available at: https://www.amazon.com/dp/B0855DXYPT/ref=sspa_dk_detail_0?pd_rd_i=B0855DXYPT&pd_rd_w=PFsy1&content-id=amzn1.sym.eb7c1ac5-7c51-4df5-ba34-ca810f1f119a&pf_rd_p=eb7c1ac5-7c51-4df5-ba34-ca810f1f119a&pf_rd_r=NBJQMF7QSPK3CYTH3K3C&pd_rd_wg=Jjaa6&p d_rd_r=80001412- (Last Visited Sep. 6, 2023).

\* cited by examiner

MEDICAL DEVICE FOR DRESSING HEAD WOUNDS

FIELD OF THE INVENTION

The present invention relates to wound care, and more particularly to head wound care. More specifically, the present invention relates to a medical device for dressing head wounds that may be worn by patients after suffering head wounds, cranial surgery, or facelift surgery.

BACKGROUND

Head wounds, including cranial wounds may occur by accident, or may be the result of necessary surgical procedures such as cranial surgery or facelift surgery. To avoid injury or infection to the treated wound and the underlying associated sensitive tissues, head wound dressings are frequently used to protect an area of a patient's head wounded either from injury or after a surgical procedure.

Existing wound dressings for head wounds have not changed over many decades. Typically, such wound dressings comprise a long strip of cloth or other appropriate bandaging, such as gauze, which is wrapped around a patient's head to form a turban-like structure. This time consuming process may take 3-5 minutes after craniotomy and 10-12 minutes following facelift surgeries. There certainly exists a learning curve to the art of proper application of traditional head dressing.

In addition to being time-consuming, conventional wrapped head dressings may become undone when applied too loosely, or when patients are uncooperative or agitated after waking up from anesthesia. In these situations, the wound dressing has to be reapplied. On the opposite extreme, if the wrapped head dressings is applied too tightly, it frequently causes significant headache and discomfort, and on rare occasions, it will result in pressure sores along the forehead or on the ear lobes.

Another type of head wound dressing is an elastic tubular dressing made of resilient materials such as rubber and/or nylon, configured in a stretch net material. Also known as "elastic tube net" bandages, the pre-cut tubular elastic stretch netting slides over a patient's head. Various pads, hot packs, cold packs, electrodes, or other medical dressings may be placed against a wound on the patient and held in place by the netting material. These dressings may be disfavored due to a lack of tensile strength, providing only minimal circumferential elasticity, thereby allowing the underlying primary dressing to shift around, exposing the underlying wound that needs to be fully covered for protection.

Other more complex devices have been created including some wound dressings systems with electronic sensors, wound dressing systems having elaborate sealing mechanisms, and arrangements having a separate connected apparatus for specialized treatments, such as thermal contrast therapy. These devices are typically intended for very specific types of injuries, and due to their complexity, are usually very expensive to manufacture.

For these reasons it is an object of the present invention to provide an easy to use, breathable head wound care bandage which can be wrapped around a patient's head within seconds, which is adaptable to a variety of wound sizes and positions, and which may be comfortably worn and used by a patient. Other objects of the present invention include providing an adaptable easy to use bandage that is inexpensive, and sufficiently resilient for prolonged periods of use, and sufficiently comfortable such that it encourages patients not to tamper with the bandage when worn. It is further an object of the present invention to provide a head wound dressing that can be adapted to provide optimal or desired focal pressure directly to the incision areas. These and other objects are more fully described in the following specification and drawings.

SUMMARY

The present invention provides a medical device for dressing head wounds of a patient. The medical device is used to dress, protect, and support the postoperative head and neck incisions following brain, ear, neck operations, and facelift procedures. The product is intended for medical purposes to function as a postoperative secondary dressing to hold a primary dressing in place, lowering the likelihood of surgical site infection, while also applying focal pressure to the underlying areas to support the surgical sites to help with the wound healing process.

The medical device is adapted to fit over the patient's head and at least partially cover the head wounds, wherein the head wounds may be located below the patient's ears and/or under the patient's chin. The medical device is adapted to accommodate at least one wound dressing pad. According to an embodiment of the present invention, the medical device may comprise a flexible cap that can be fit over the patient's head. The flexible cap comprises a head covering dome and a circumferential adjustable headband. The head covering dome has an apex and a circumferential baseline. The circumferential adjustable headband is affixed to the circumferential baseline of the head covering dome. The circumferential adjustable headband may be adapted to adjustably fold over the head covering dome to create a circumferential pocket. The circumferential adjustable headband is adapted to surround the patient's head at least partially below the patient's ears, and the circumferential pocket may be configured to accommodate the at least one wound dressing pad for covering the head wounds, wherein the head wounds are located in front, back, and/or below the patient's ears.

The medical device may further comprise an adjustable strap. The adjustable strap may comprise an elongated body having two opposite ends. The two opposite ends are adapted to be coupled to the head covering dome using an attachment mechanism, and the adjustable strap can be further adapted to cover the patient's chin, thereby securing the flexible cap over the patient's head. The adjustable strap may further comprise a chin pocket, wherein the chin pocket is formed at a middle portion of the elongated body such that it overlays at least a portion of the patient's chin, and the chin pocket is adapted to accommodate the at least one wound dressing pad for covering a wound on the patient's chin.

According to an implementation of the invention, the elongated body of the chin strap can be made of two layers of material, wherein the two layers are affixed to each other at their edges, and the chin pocket is formed between the two layers. The chin pocket may be formed across the middle third of the elongated body. In an embodiment of the invention, the head covering dome of the cap may comprise a single-layer material, and the headband may comprise a double-layered material. The attachment mechanism for coupling the chin strap to the head covering dome can be a hook and loop fastener.

The present invention further provides methods of dressing head wounds of a patient using the medical devices according to various embodiments of the present invention, wherein the medical device comprises a flexible dome-shaped cap and an adjustable chin strap, the flexible dome-shaped cap has an adjustable circumferential pocket around its base, the adjustable chin strap has two opposite ends and a chin pocket, and the medical device is adapted to accommodate at least one wound dressing pad.

The method may comprise the steps of fitting the flexible dome-shaped cap over the patient's head; adjusting the adjustable circumferential pocket to surround the patient's head at least partially below the patient's ears; and inserting the at least one wound dressing pad into the adjustable circumferential pocket for covering the head wounds, wherein the head wounds are located at least partially below the patient's ears.

The method may further comprise the steps of covering at least a portion of the patient's chin using the chin pocket; inserting the at least one wound dressing pad into the chin pocket covering the head wounds, wherein the head wounds are further located on the at least a portion of the patient's chin; and coupling the two opposite ends of the adjustable chin strap to the flexible dome-shaped cap, thereby securing the chin strap over the patient's chin.

In this method, the step of coupling the two opposite ends of the adjustable chin strap to the flexible dome-shaped cap may further comprise the step of adjusting the chin strap to provide a desired focal pressure on the at least the portion of the patient's chin. The method may further comprise the step of monitoring recovery of the head wounds, and replacing the at least one wound dressing pad. The method may further comprise the steps of covering the head wounds by the chin pocket (and wound dressing pads inserted thereto), wherein the head wounds are created as a result of a facelift surgery; and covering the head wounds by the circumferential pocket (and wound dressing pads inserted thereto), wherein the head wounds are created as the result of the facelift surgery.

According to another embodiment of the invention, the invention provides a medical device for dressing head wounds of a patient. The medical device is adapted to fit over the patient's head and at least partially cover the head wounds, wherein the head wounds may be located below the patient's ears and/or under the patient's chin. The medical device is adapted to accommodate at least one wound dressing pad. The medical device may comprise a flexible cap that can be fit over the patient's head; the flexible cap may comprise a head covering dome and a circumferential adjustable headband; the head covering dome may have an apex and a circumferential baseline; the circumferential adjustable headband can be affixed to the circumferential baseline of the head covering dome; the circumferential adjustable headband can be adapted to adjustably fold over the head covering dome to create a circumferential pocket; the circumferential adjustable headband can be adapted to partially surround the patient's head at least partially below the patient's ears. The medical device may further comprise an adjustable strap having two opposite ends; the two opposite ends are adapted to be affixed to the flexible cap using an attachment mechanism, the adjustable strap can be further adapted to cover the patient's chin, thereby securing the flexible cap over the patient's head. The adjustable strap may further comprise a chin pocket, wherein the chin pocket is formed at a middle portion of the adjustable strap such that it overlays the patient's chin; and the circumferential pocket and the chin pocket can be configured to accommodate the at least one wound dressing pad for covering the head wounds, wherein the head wounds are located at least partially below the patient's ears and at least partially on the patient's chin. The adjustable strap can be made of two layers of material, wherein the two layers are affixed to each other at their edges, and the chin pocket is formed between the two layers. The chin pocket can be formed across the middle third of the adjustable strap, and the attachment mechanism can be a hook and loop fastener.

DESCRIPTION

The present invention is described more fully hereinafter, but not all embodiments are shown. While the invention has been described with reference to exemplary embodiments, it will be understood by those skilled in the art that various changes may be made, and equivalents may be substituted for elements thereof without departing from the scope of the disclosure. In addition, many modifications may be made to adapt a particular structure or material to the teachings of the disclosure without departing from the essential scope thereof.

The drawings accompanying the application are for illustrative purposes only. They are not intended to limit the embodiments of the present application. Additionally, the drawings are not drawn to scale. Common elements between different figures may retain the same numerical designation.

Figure 1:
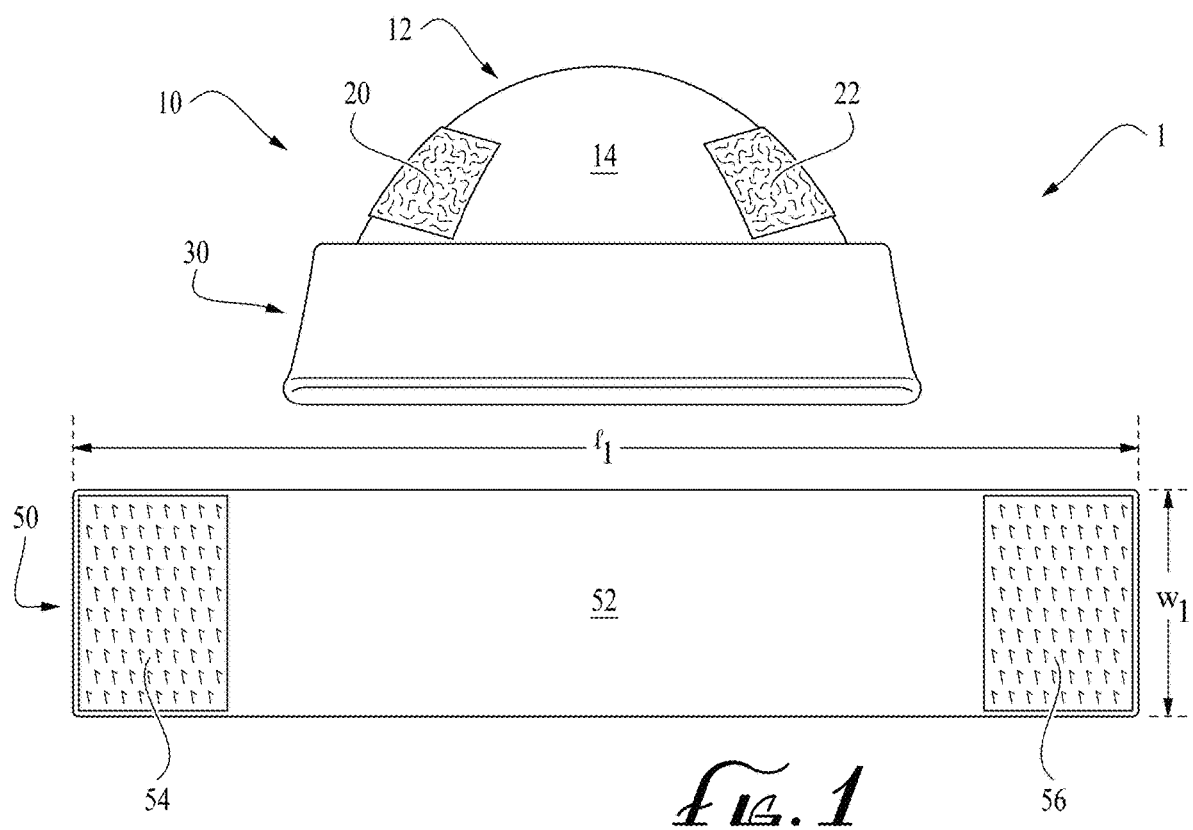
FIG. 1 illustrates a front elevation view of a cap and a top view of a chin strap, wherein the cap and the chin strap form a medical device for dressing head wounds.

Referring to FIG. 1, the figure illustrates a front elevation view of the flexible cap ("cap") 10 and a top view of the chin strap 50, wherein the cap and the chin strap form a medical device 1 for dressing head wounds. The medical device 1 for dressing head wounds comprises a flexible cap ("cap") 10 and a chin strap 50. The cap 10 is configured in the shape of a conventional skull cap which is designed to fit over a patient's head (not shown). The cap 10 includes the head covering dome portion ("dome") 12 and the headband portion ("headband") 30. The dome 12 is configured such that it covers a patient's head, while the headband 30 is configured to surround the patient's head, at, over, or below the patient's ears.

Figure 4:
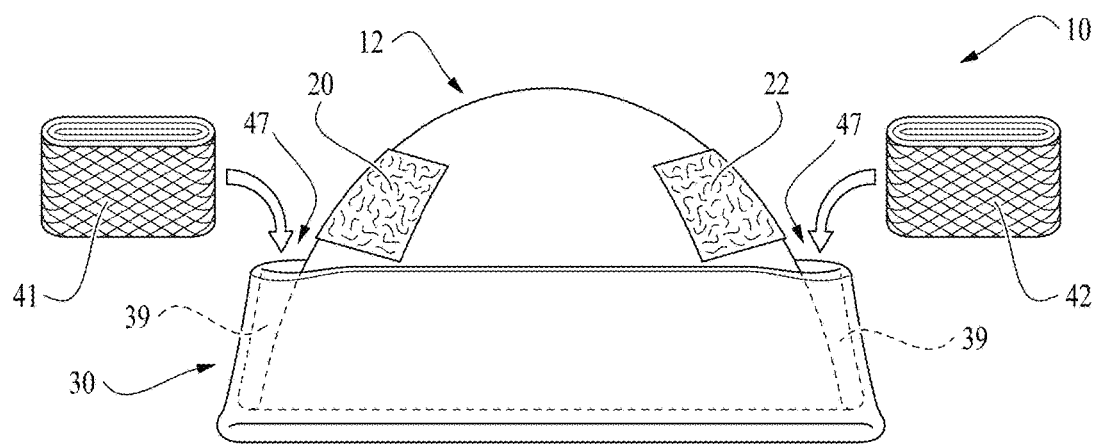
FIG. 4 illustrates a front elevation view of the cap with the headband in its folded position.
Figure 5:
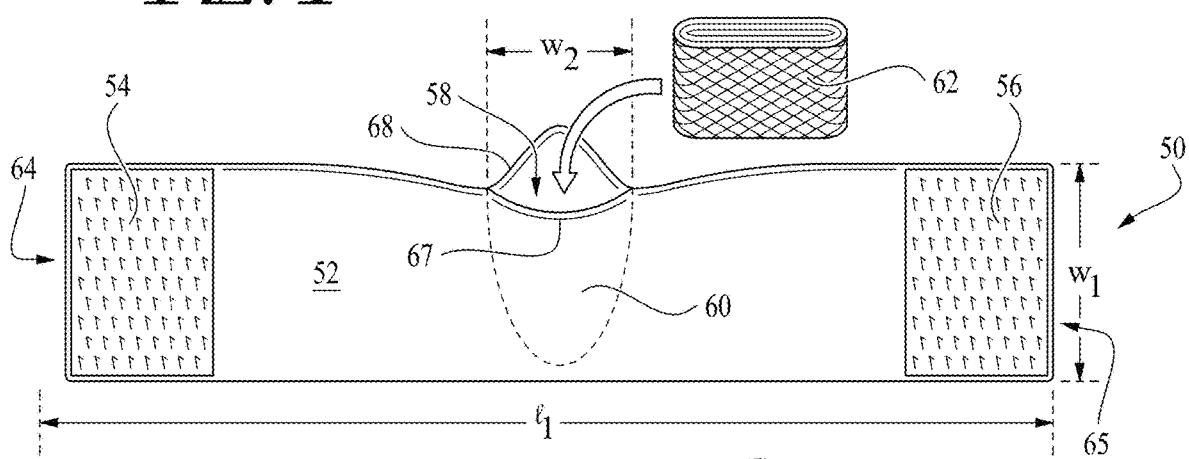
FIG. 5 illustrates a top view of the chin strap with a small chin pocket created at the middle portion of the chin strap.

Still referring to FIG. 1, the chin strap 50 comprises the elongated body 52 having a length (l1) and a width (w1). The chin strap 50 can be coupled to the cap 10 through an attachment mechanism. In an implementation of the invention, the attachment mechanism can be an easy on/off Velcro® closure which allows a user to adjustably couple the chin strap to the cap to provide further dressing for head wounds and prevent dressing failure (slippage) requiring re-application of the medical device. As a non-limiting example, the attachment mechanism can be a set of hook and loop fasteners comprising hooks 54 and 56 (as shown in FIG. 5) that can be coupled to their corresponding loops 22 and 20 (as shown in FIG. 4) respectively.

The material comprising the medical device 1 is preferably a soft cotton-like material having absorption and breathability characteristics. Existing wound dressings are typically made of 100% cotton material. Although such a material may be used in one embodiment of the present invention, it is preferred that a mixture of cotton and elastic fiber (for example an elastane such as Spandex® or Lycra®) material is used for better circumferential elasticity. In one preferred embodiment, a blend of 95% cotton and 5% elastic fiber material may be used to provide a breathable fabric material with optimal, evenly distributed, circumferential elasticity to maximize comfort.

Figure 2:
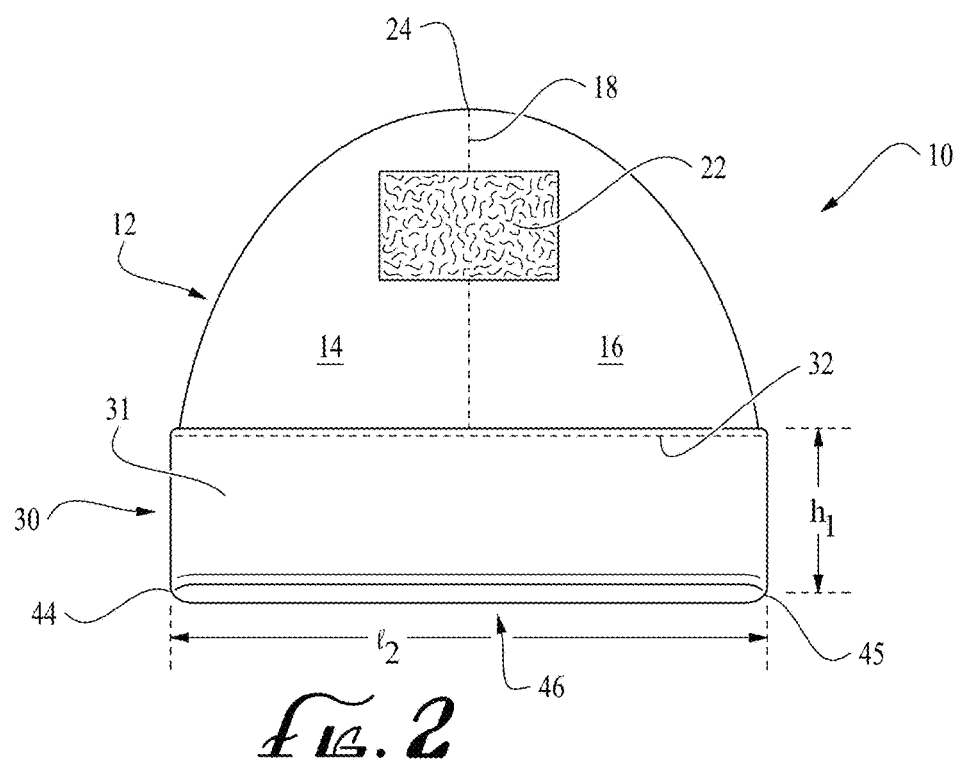
FIG. 2 illustrates a side elevation view of the cap with a headband in its unfolded position.

Referring to FIG. 2, the figure illustrates a side elevation view of the cap 10 with the headband 30 in its unfolded position. The cap 10 has a bottom opening 46 through which a patient's head (not shown) extends when the cap 10 is applied to a wound and while the cap 10 is worn. The dome portion 12 and the headband 30 of the cap 10 are preferably made of two complementary matching sections or pieces. As illustrated, the dome is substantially hemispherical. The dome portion 12 may comprise a hemispherical first dome section 14 and a substantially similar hemispherical matching (i.e., "mirror image") second dome section 16. The first dome section 14 and the second dome section 16 are configured such that when they are connected by the seam 18, the overall dome-like structure of the dome 12 is formed. In one preferred embodiment, the dome 12 may comprise a single layer of material, while the headband 30 may comprise a "two ply" or double layered material. The headband 30 may comprise the elongated body 31 having two opposite ends, wherein the two opposite ends are connected to form the overall band-like structure of the circumferential headband 30. The headband 30 is connected to the base of the dome 12 by the seam 32.

Still referring to the illustrated embodiment of FIG. 2, when laid flat, the headband 30 has the length (l2) that is defined between the front end 44 to the back end 45. The length (l2) can be approximately 9.5 inches from the front end 44 to the back end 45. The headband 30 has the height (h1). The height (h1) can be preferably approximately 3 inches in height, and the dome 12 preferably extends approximately 6.25 inches above the headband 30 at its apex 24. Although these are one set of preferred dimensions, it is contemplated that any other dimensions which are suitable for resilient installation over the head of a patient may be employed, such as modifying the cap 10 and headband 30 to be much smaller, so that it can be used by children and infants.

In an implementation of this invention, the cap 10 may include pockets for holding wound dressing pads. The pockets can be designed to hold the wound dressing pads securely in place, in virtually any cranial position preferred by a treating physician or nurse. Wound dressing pads may be inserted in the pockets to provide optimal or desired focal pressure directly to the incision area.

Figure 3:
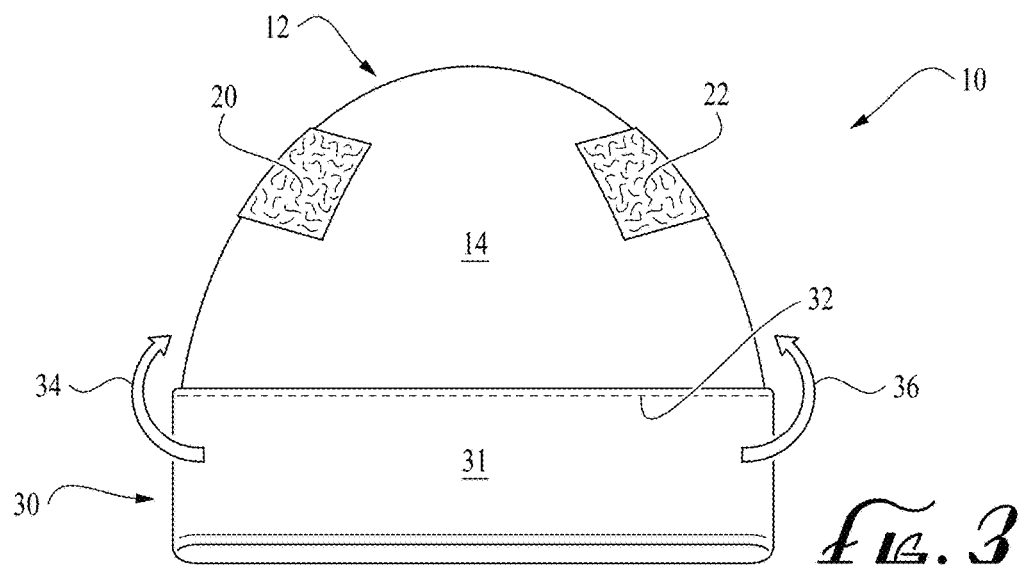
FIG. 3 illustrates a front elevation view of the cap wherein the headband in its unfolded position.

Referring to FIGS. 3-4, the cap 10 is adapted to accommodate wound dressing pads (41 and 42). The dome 12 and the headband 30 (when folded over the dome 12) together define the pocket opening 47 into which one or more wound dressing pads may be inserted. As shown by arrows 34 and 36 (as shown in FIG. 3), the headband 30 can be folded up over the dome 12 to make a circumferential pocket 39 (as shown in FIG. 4) to accommodate wound dressing pads (41 and 42). According to FIG. 4 and as further illustrated in FIG. 8, the pads (41, 42) can be inserted into the pocket 39 to further cover the head wounds. The size of the pocket 39 can be adjusted by folding more or less of the headband 30 over the dome 12. Furthermore, as the dome 12 and headband 30 can be made of a flexible material, the headband 30 can be configured to surround the patient's head, at, over, or below the patient's ears. As a non-limiting example, the circumferential pocket 39 can be adapted to accommodate pads (such as the pads 41 and 42) for covering the head wounds, wherein the head wounds are at least partially located below the patient's ears or in proximity of the patient's ears.

According to FIG. 4, as the circumferential pocket 39 extends all the way around the dome 12, wound dressings, such as a pad or other wound care material, with different sizes can be used to cover the head wounds located in proximity of the circumferential pocket 39. In an implementation of the invention, the internal and external walls of the circumferential pocket 39 may comprise a natural or synthetic material, including a breathable, mesh material, and may also comprise an absorbent wound dressing material, such that the circumferential pocket walls can effectively form a part of the wound dressing. In some other embodiments, the material itself of the circumferential pocket walls may be sufficient to dress and cover a patient's head wound.

In some preferred embodiments, the dome 12 as well as the headband 30 are made of an elastic material to accommodate a variety of sizes and thicknesses of wound dressing pads. In other preferred embodiments, the headband 30 can be made of an elastic material with sufficient resiliency to hold the dome 12 (and any wound dressing pads) firmly in place against the patient's head.

Figure 7:
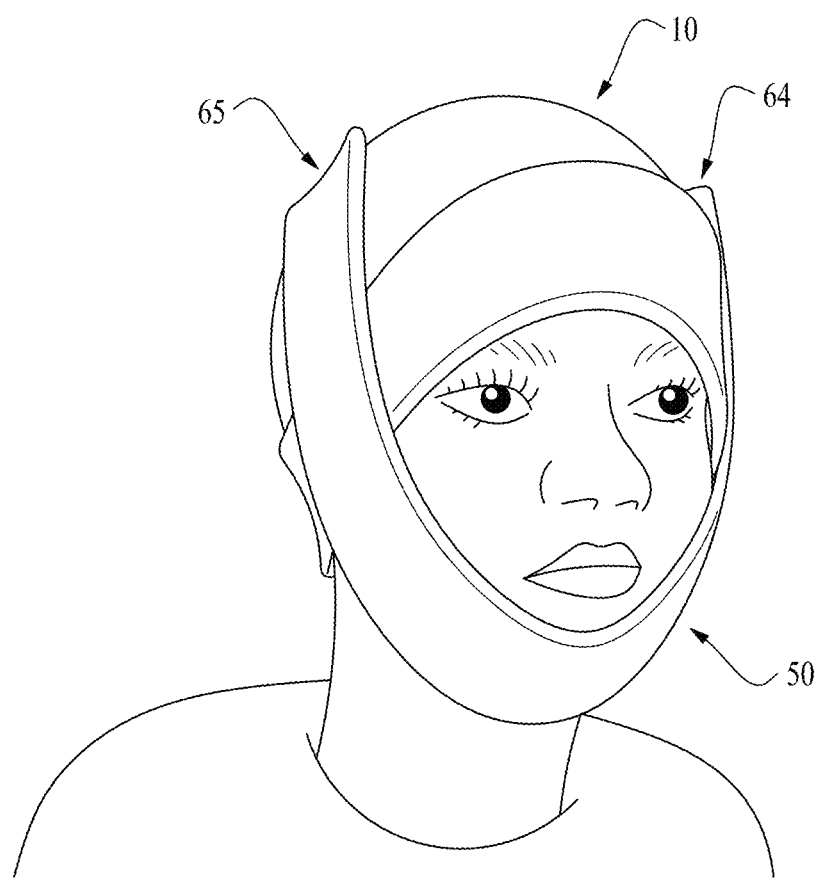
FIG. 7 illustrates a perspective view of the cap and the chin strap worn by the patient.

Referring to FIG. 5, the figure illustrates the chin strap 50 comprising the elongated body 52 having two opposite ends (64, 65). The elongated body 52 has the length (l1) and the width (w1). The chin strap 50 can be coupled to the head covering dome 12 of the cap 10 through an attachment mechanism (54 and 56) that is coupled to the two opposite ends (64, 65) of the chin strap 50. The attachment mechanism can be a set of hook and loop fasteners. As a non-limiting example, the attachment mechanism can be a set of hook and loop fasteners comprising hooks 54 and 56 (as shown in FIG. 5) that can be coupled to their corresponding loops 22 and 20 (as shown in FIG. 4) respectively. The chin strap 50 can be a flexible adjustable strap. The chin strap 50 further comprises the chin pocket 60 having the opening 58 and the width (w1). The chin pocket 60 is formed at a middle portion of the elongated body 52. When the chin strap 50 is coupled to the cap 10 (as shown in FIG. 7), the chin pocket 60 may overlay at least a portion of the patient's chin. The chin pocket 60 has the width (w2). The length (l1) can be approximately 16.5 inches, the width (w1) can be approximately 3.5 inches, and the width (w2) can be approximately 2.5 inches. Although these are one set of preferred dimensions, it is contemplated that any other dimensions which are suitable for resilient installation over the head and chin of a patient may be employed, such as modifying the chin strap 50, so that it can be used by children.

Still referring to FIG. 5, according to an implementation of this embodiment, the chin pocket 60 can accommodate at least one wound dressing pad such as the pad 62 for covering at least a portion of the head wound (not shown) on the patient's chin. Wound dressing pads may be inserted in the chin pocket to provide optimal or desired focal pressure directly to an incision area.

As illustrated in FIG. 5, the elongated body 52 can be made of two layers (67, 68) of material, wherein the two layers (67, 68) are affixed to each other at their edges, and the chin pocket 60 is formed between the two layers. In a preferred embodiment of the invention, the chin pocket 60 is formed across the middle third portion of the elongated body.

Figure 6:
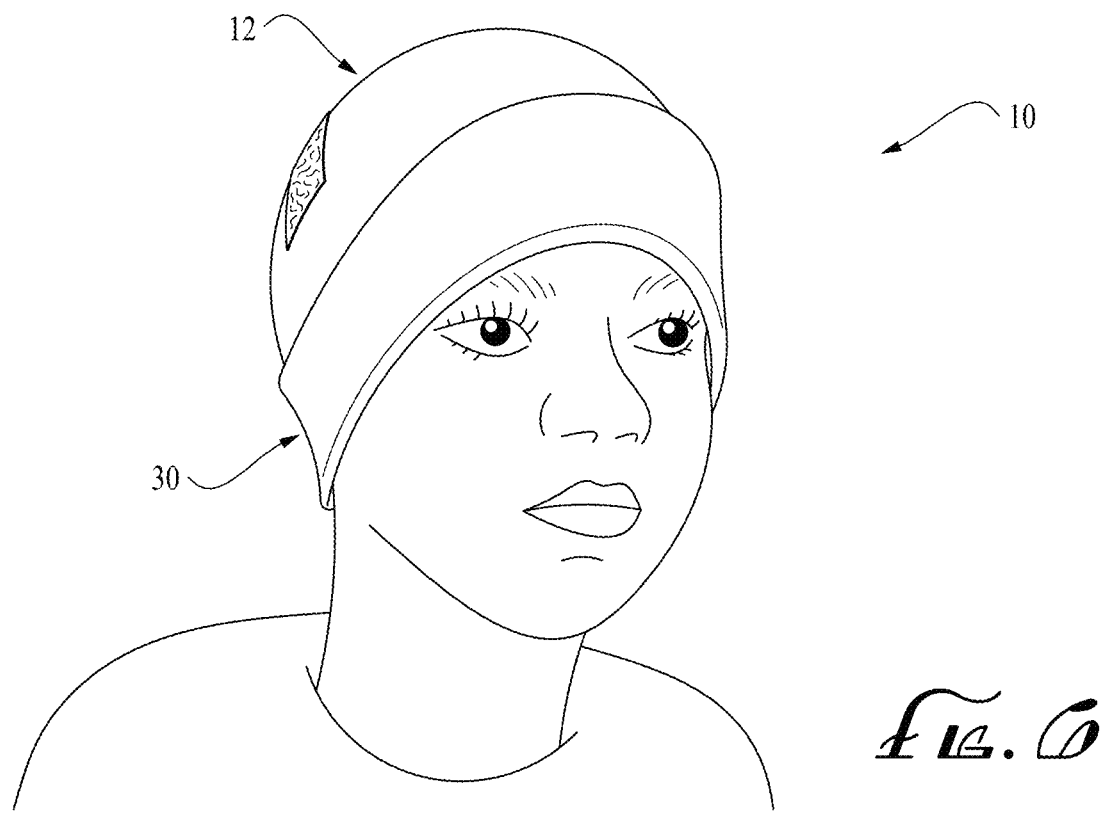
FIG. 6 illustrates a perspective view of the cap worn by a patient.

The invention further provides methods of dressing head wounds using the medical device 1 (as shown in FIG. 1 and further illustrated in FIGS. 2-10). In order to use the cap 10 and the chin strap 50, a treating physician or nurse will first observe the patient, and determine the type of dressing needed based on the size and extent of the patient's head injury. According to a method of practicing the invention, as shown in FIG. 6, the method comprises the steps of fitting the cap 10 over the patient's head; and adjusting the circumferential pocket 39 (the circumferential pocket 39 is shown in FIG. 4) to cover at least a portion of the patient's head. In this step, after securing a layer of sterile gauze directly over the incision (not shown), the cap 10 is lowered over the patient's head. The dome 12 and the headband 30 are brought down around the patient's head, and then the headband 30 is released, thereby providing a secure, appropriately snug head wound dressing. As illustrated in FIG. 6, the headband 30 can be folded over the dome 12 to create an adjustable circumferential pocket to cover a portion of the patient's head at least partially below the patient's ears. The headband 30 can be folded over the dome 12 before or after lowering down the cap 10 over the patient's head. After fitting the cap 10 over the patient's head, the size of the circumferential pocket in different locations around the dome 12 can be further adjusted by changing the fold size of the headband 30 in the different locations. In an implementation of the method, after fitting the cap 10 over the patient's head, the headband 30 may be folded to optimally fit the patient's head size, and the remaining fold of the headband 30 may serve as the circumferential pocket for placement of wound dressing pad(s), as needed or desired, for application of focal pressure over the surgical incisions.

Figure 8:
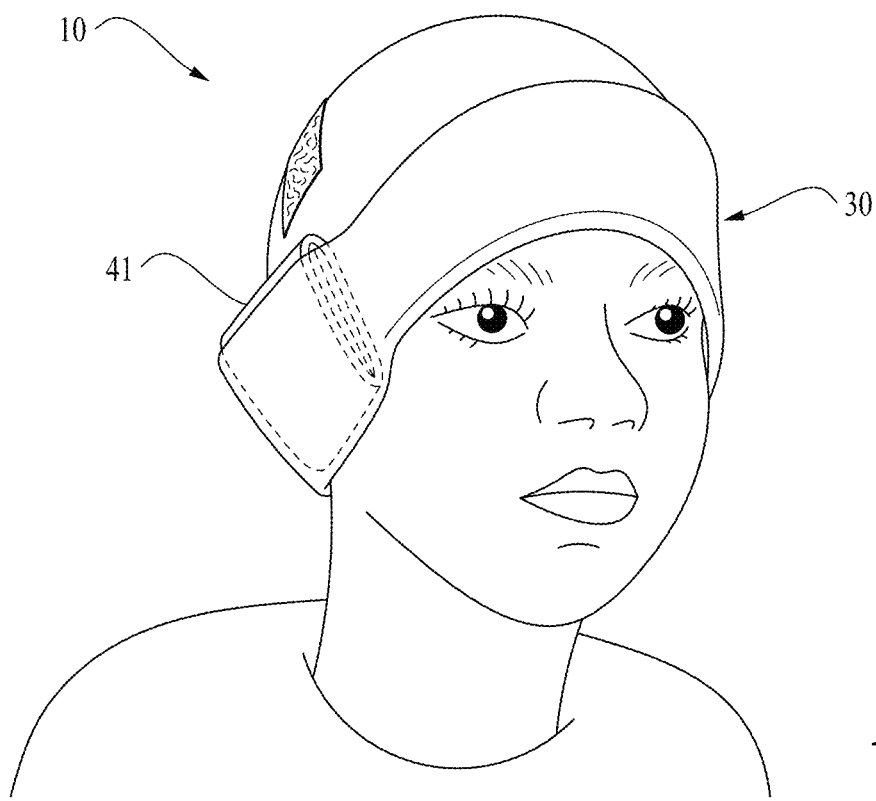
FIG. 8 illustrates a perspective view of the cap when a wound dressing pad is inserted into a circumferential pocket.

The method may further comprise the step of inserting wound dressing pads into the adjustable circumferential pocket 39 (such as the pads 41 and 42 as shown in FIG. 4) to cover the head wounds that are located at least partially below the patient's ears. The wound dressing pads may be inserted into the circumferential pocket of the cap 10 before fitting the cap 10 over the patient's head. In the alternative, the wound dressing pads may be inserted into the circumferential pocket of the cap 10 after the cap 10 and the headband 30 are held in place over the patient's head. A general view of the cap 10 with the pad 41 inserted into the circumferential pocket is illustrated in FIG. 8.

Figure 9:
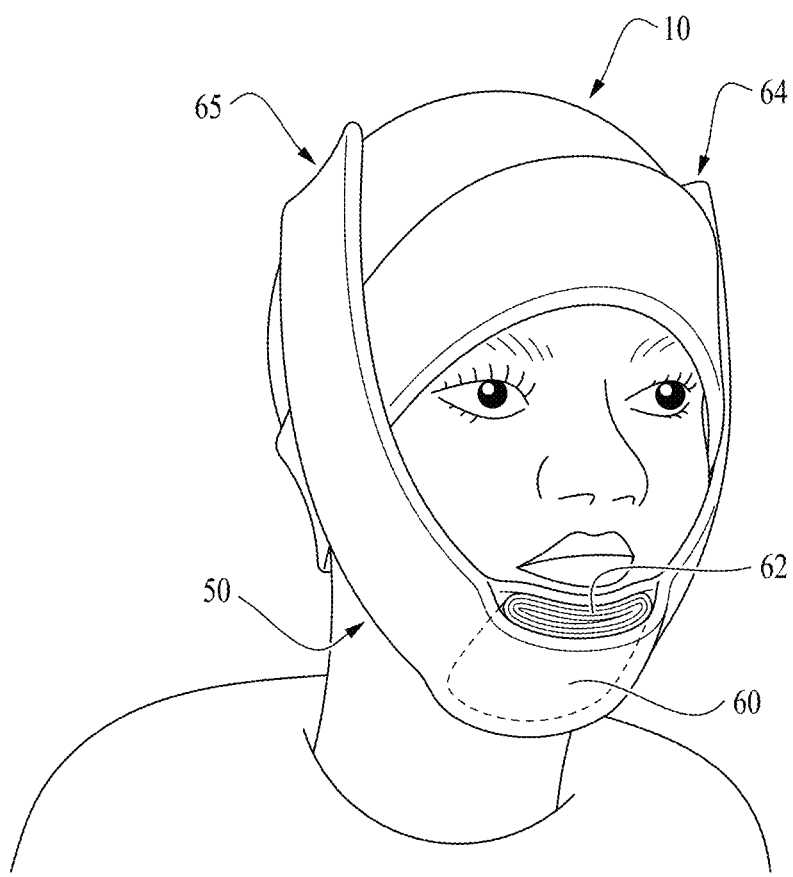
FIG. 9 illustrates a perspective view of the cap and the chin strap when a wound dressing pad is inserted into the chin pocket.

According to FIG. 9, the method may further comprise the steps of covering at least a portion of the patient's chin using the chin strap 50 such that the chin pocket 60 overlays the at least a portion of the patients chin; inserting at least one wound dressing pad (such as the pad 62) into the chin pocket 60 covering the head wounds (not shown), wherein the head wounds are located on the at least a portion of the patient's chin; and coupling the two opposite ends (64, 65) of the chin strap 50 to the cap 10, thereby securing the chin strap over the patient's chin. In this method, the tension of the chin strap can be adjusted by an attachment mechanism, such as a hook and loop fastener, to provide a desired focal pressure on the at least a portion of the patient's chin. In an implementation of the invention as shown in FIGS. 5-6, in some instances of moderate injury, or if otherwise appropriate, the circumferential pocket and the chin pocket may be left empty, and the material of the cap 10 and the chin strap 50 may be sufficient to dress and cover the head wounds without using any additional wound dressing pad.

The method may further comprise the steps of monitoring recovery of the head wounds, and replacing the wound dressing pads (such as the pads 41-42 and 62 as shown in FIGS. 4-5). In an implementation of the method, the method can be used for covering the head wounds created on at least a portion of the patient's chin or in proximity of the patient's chin such as the wounds created under the patient's chin as a result of the incisions in a facelift surgery, and/or the wounds created at least partially in proximity of the patient's ears such as the wounds created in front, back, and/or below the patient's ears as a result of the incisions in a facelift surgery.

In various implementation of the method of dressing head wounds as discussed above, additional steps may be performed with respect to the described methods. Additionally or alternatively, certain steps of the described methods may be removed, modified, performed in a different order, or a combination thereof. Further still, the steps of any of the respective methods may be performed in parallel with one another, such as at the same time, and/or the step(s) of one of the methods may be performed in response to initiation or completion of the step(s) of another one of the methods.

Figure 10:
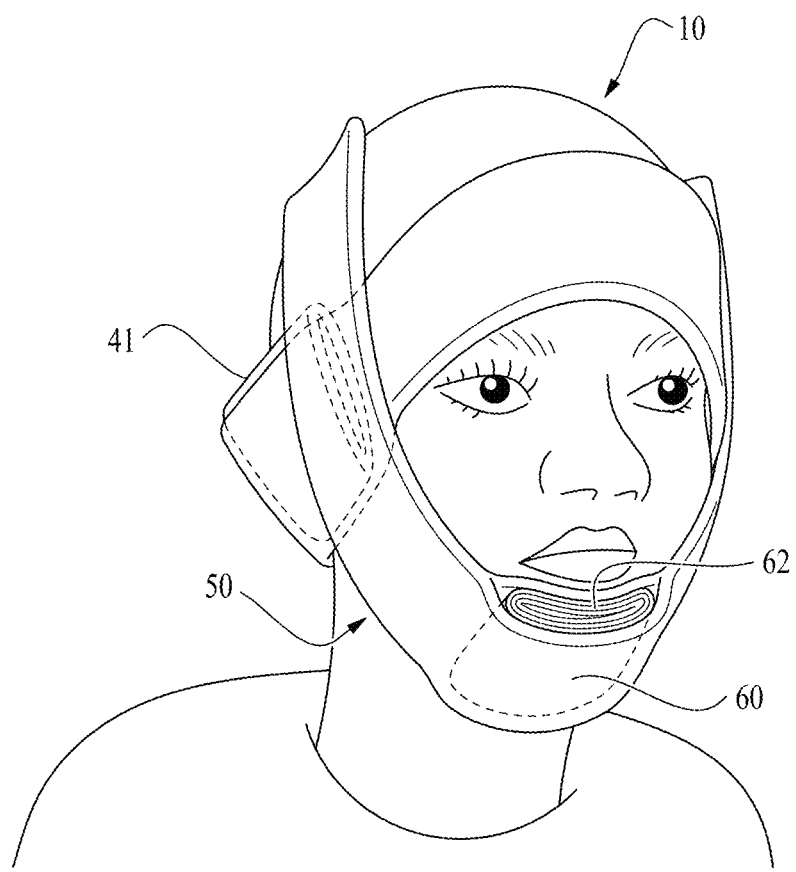
FIG. 10 illustrates a perspective view of the cap and the chin strap when a wound dressing pad is inserted into the circumferential pocket and another wound dressing pad is inserted into the chin pocket.

FIG. 10 illustrates a general view of the invention wherein the cap 10 and the chin strap 50 are coupled together and are fit over the patient's head, thereby holding the wound dressing pads (such as the pads 41 and 62, and other pads as needed) in place.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claim.

What is claimed is:

1. A medical device for dressing head wounds of a head of a patient, the medical device adapted to fit over the head of the patient and at least partially cover the head wounds, wherein some of the head wounds are located below ears of the patient and/or under a chin of the patient, the medical device adapted to accommodate at least one wound dressing pad, the medical device comprising:

a flexible cap adapted to fit over the head of the patient;

the flexible cap comprising a head covering dome and a circumferential adjustable headband;

the head covering dome comprising an apex and a circumferential baseline;

wherein the circumferential adjustable headband is affixed to the circumferential baseline of the head covering dome;

the circumferential adjustable headband is adapted to adjustably fold over the head covering dome to create a circumferential pocket;

the circumferential adjustable headband is adapted to partially surround the head of the patient at least partially below the ears of the patient;

the circumferential pocket is configured to accommodate the at least one wound dressing pad for covering the head wounds, wherein the head wounds are located below the ears of the patient; and an adjustable strap comprising an elongated body comprising two opposite ends adapted to be coupled to the head covering dome at corresponding locations of the head covering dome between the apex of the head covering dome and the circumferential pocket using an attachment mechanism, and configured to overlay the circumferential pocket, wherein the flexible cap is adapted to be fit over the head of the patient and the adjustable strap is configured to be coupled to the flexible cap and at least partially extend under the chin of the patient to hold the at least one wound dressing pad in place relative to the head of the patient.

2. The medical device of claim 1, wherein the attachment mechanism comprises a first attachment mechanism adapted to couple a first end of the two opposite ends of the elongated body of the adjustable strap to the head covering dome, and the attachment mechanism comprises a second attachment mechanism adapted to couple a second end of the two opposite ends of the elongated body of the adjustable strap to the head covering dome.

3. The medical device of claim 2, wherein the first attachment mechanism comprises a first part attached to the head covering dome at a first location of the corresponding locations of the head covering dome, and the first end of the elongated body of the adjustable strap comprises a second part of the first attachment mechanism adapted to be releasably attached to the first part to releasably couple the first end of the elongated body to the head covering dome at the first location; and the second attachment mechanism comprises a first part attached to the head covering dome at a second location of the corresponding locations of the head covering dome, and the second end of the elongated body of the adjustable strap comprises a second part of the second attachment mechanism adapted to be releasably attached to the first part of the second attachment mechanism to releasably couple the second end of the elongated body to the head covering dome at the second location.

4. The medical device of claim 3, wherein the first attachment mechanism comprises a hook and loop fastener and the second attachment mechanism comprises a hook and loop fastener.

5. The medical device of claim 1, wherein the adjustable strap further comprises a chin pocket formed by two overlapping layers of material of the elongated body of the adjustable strap affixed to each other at edges of the elongated body with an opening formed at a middle portion of the elongated body to access the chin pocket; and the chin pocket adapted to accommodate the at least one wound dressing pad for covering at least a portion of a wound on the chin of the patient.

6. The medical device of claim 5, wherein the chin pocket is formed across a middle third of the elongated body.

7. The medical device of claim 1, wherein the head covering dome comprises a single-layer material, and the headband comprises a double-layered material extending circumferentially around the outside of the head covering dome.

8. The medical device of claim 1, wherein the attachment mechanism comprises a hook and loop fastener.

9. A method of dressing head wounds located at least partially below ears of a head of a patient comprising:

fitting a flexible dome-shaped cap over the head of the patient, wherein the flexible dome-shaped cap comprises an adjustable circumferential pocket extending around a base of the flexible dome-shaped cap;

adjusting the adjustable circumferential pocket to surround the head of the patient at least partially below the ears of the patient;

inserting a wound dressing pad into the adjustable circumferential pocket; and securing the flexible dome-shaped cap to the head of the patient with an adjustable strap by extending an elongated body of the adjustable strap under a chin of the patient, coupling a first end of the elongated body to a dome of the dome-shaped cap at a first location of the dome between an apex of the dome and the circumferential pocket, and coupling a second end of the elongated body to the dome at a second location of the dome between the apex of the dome and the circumferential pocket.

10. The method of claim 9, further comprising:

covering at least a portion of the chin of the patient by a chin pocket formed by two overlapping layers of material of the elongated body of the adjustable strap affixed to each other at edges of the elongated body with an opening formed at a middle portion of the elongated body to access the chin pocket;

inserting at least one wound dressing pad into the chin pocket to cover a head wound located on at least a portion of the chin of the patient, wherein coupling a first end of the elongated body to the dome of the dome-shaped cap at the first location above the circumferential pocket and above the first ear of the patient, and coupling the second end of the elongated body to the dome at the second location above the circumferential pocket and above the second ear of the patient secures the adjustable strap over the chin of the patient.

11. The method of claim 10, wherein the step of coupling the two opposite ends of the adjustable strap to the flexible dome-shaped cap further comprises;

adjusting the strap to provide a desired focal pressure on the at least the portion of the chin of the patient.

12. The method of claim 11, further comprising covering the head wounds by the chin pocket, wherein the head wounds are created as a result of a facelift surgery.

13. The method of claim 12, further comprising covering the head wounds by the circumferential pocket, wherein the head wounds are created as the result of the facelift surgery.

14. The method of claim 11, further comprising monitoring recovery of the head wounds, and replacing the at least one wound dressing pad.

15. The method of claim 9, wherein a first part of a first attachment mechanism is attached to the dome at the first location, a first part of a second attachment mechanism is attached to the dome at the second location, the first end of the elongated body of the adjustable strap comprises a second part of the first attachment mechanism, the second end of the elongated body of the adjustable strap comprises a second part of the second attachment mechanism, and wherein coupling the first end of the elongated body to the dome at the first location comprises releasably attaching the second part of the first attachment mechanism of the first end of the elongated body of the adjustable strap to the first part of the first attachment mechanism at the first location of the dome, and coupling the second end of the elongated body to the dome at the second location comprises releasably attaching the second part of the second attachment mechanism of the second end of the elongated body of the adjustable strap to the first part of the second attachment mechanism at the second location of the dome.

16. The method of claim 15, wherein the first attachment mechanism comprises a hook and loop fastener and the second attachment mechanism comprises a hook and loop fastener.

17. The method of claim 9, wherein the elongated body of the adjustable strap comprises a chin pocket formed by two overlapping layers of material affixed to each other at edges of the elongated body with an opening formed at a middle portion of the elongated body to access the chin pocket.

18. The method of claim 9, wherein coupling a first end of the elongated body to the first location of the dome, and coupling the second end of the elongated body to the second location of the dome extends the elongated body of the adjustable strap at least partially over the wound dressing pad while the wound dressing pad is inserted within the adjustable circumferential pocket to hold the wound dressing pad in place within the adjustable circumferential pocket.

19. A medical device for dressing head wounds of a head of a patient, the medical device adapted to fit over the head of the patient and at least partially cover the head wounds, wherein some of the head wounds are located below ears of the patient, the medical device adapted to accommodate at least one wound dressing pad, the medical device comprising:
- a flexible cap adapted to fit over the head of the patient;
- the flexible cap comprising a head covering dome and a circumferential adjustable headband;
- the head covering dome comprising an apex and a circumferential baseline;
- wherein the circumferential adjustable headband is affixed to the circumferential baseline of the head covering dome;
- the circumferential adjustable headband is adapted to adjustably fold over the head covering dome to create a circumferential pocket;
- the circumferential adjustable headband is adapted to surround the head of the patient at least partially below the ears of the patient;
- the circumferential pocket is configured to accommodate the at least one wound dressing pad for covering at least one the head wound;
- an adjustable strap comprising an elongated body comprising two opposite ends configured to be coupled to the head covering dome above the circumferential pocket while the elongated body is configured to overlay the circumferential pocket and at least partially extend under the chin of the patient, wherein a first end of the two opposite ends is adapted to be coupled to the head covering dome above the circumferential pocket using a first attachment mechanism, a second end of the two opposite ends is adapted to be coupled to the head covering dome above the circumferential pocket using a second attachment mechanism;
- the first attachment mechanism comprises a first part attached to the head covering dome at a first location between the apex of the head covering dome and an opening into the circumferential pocket, and the first end of the elongated body of the adjustable strap comprises a second part of the first attachment mechanism adapted to be releasably attached to the first part to releasably couple the first end of the elongated body to the head covering dome at the first location; and
- the second attachment mechanism comprises a first part attached to the head covering dome at a second location between the apex of the head covering dome and an opening into the circumferential pocket, and the second end of the elongated body of the adjustable strap comprises a second part of the second attachment mechanism adapted to be releasably attached to the first part of the second attachment mechanism to releasably couple the second end of the elongated body to the head covering dome at the second location.

20. The medical device of claim 19, wherein the first attachment mechanism comprises a hook and loop fastener and the second attachment mechanism comprises a hook and loop fastener.

* * * * *